United States Patent [19]
Hursman et al.

[11] Patent Number: 6,004,305
[45] Date of Patent: Dec. 21, 1999

[54] DRAINAGE CATHETER ASSEMBLY

[75] Inventors: Thomas L. Hursman, Diamond Bar, Calif.; Robert H. Waechter, Scottsdale, Ariz.

[73] Assignee: Spectrum Medsystems, Inc., Irvine, Calif.

[21] Appl. No.: 08/642,269

[22] Filed: May 3, 1996

[51] Int. Cl.⁶ ....................................................... A61F 5/44
[52] U.S. Cl. ........................ 604/328; 604/326; 604/349; 128/761
[58] Field of Search ..................................... 604/264, 349, 604/352, 331, 326, 320; 128/761, 760

[56] References Cited

U.S. PATENT DOCUMENTS

| | | | |
|---|---|---|---|
| 4,652,259 | 3/1987 | O'Neil | 604/54 |
| 5,147,341 | 9/1992 | Starke et al. | 604/349 |
| 5,454,798 | 10/1995 | Kubalok et al. | 604/349 X |

OTHER PUBLICATIONS

"Dow Corning© 360 Medical Fluid", Product Info. 1995 Dow Corning Corporation (4 pages).
"Manager Industries, Inc.", Product Designation: MP–110 Jan. 15, 1993 (2 pages).
"Kenpak" Medical Pakaging Specialists, Kenpak Product Designation (1 page).

*Primary Examiner*—Mark Bockelman
*Assistant Examiner*—N. Kent Gring
*Attorney, Agent, or Firm*—Stout, Uxa, Buyan & Mullins, LLP

[57] ABSTRACT

A catheter assembly for draining and collecting fluid from a body cavity has a container having an inner containment space defined therewith. An elongate tubular catheter extends longitudinally through the container. A tip member/lubricant reservoir is mounted to the catheter passage opening. A quantity of lubricant is disposed within a tip member/lubricant reservoir and lubricate the catheter as it is extended from the container.

9 Claims, 4 Drawing Sheets

DRAINAGE CATHETER ASSEMBLY

FIELD OF THE INVENTION

This invention relates generally to medical devices and more particularly to drainage catheter assemblies for draining fluid from body cavities, such as the urinary bladder or gastrointestinal tract.

BACKGROUND OF THE INVENTION

Various self-contained drainage catheter assemblies have been known in the prior art. Such drainage catheter assemblies typically comprise flexible catheters having plastic collection bags connected thereto. The flexible catheter is insertable into a body orifice or passageway (e.g., urethra) such that fluid may drain through the lumen of the catheter and into the attendant collection bag.

Examples of drainage catheter assemblies of the prior art are found in U.S. Pat. Nos. 4,652,259 (O'Neill) and 5,147,341 (Starke et al).

Although the self-contained drainage catheter assemblies of the prior art have become commonly used in clinical practice, especially for intermittent or long term catheterization of the urinary bladder, these prior art-drainage catheter assemblies have been of designs and configurations which are less than optimal for all applications. Accordingly, there remains a need in the art for the development of improved self-contained drainage catheter assemblies which incorporate modified designs and configurations to provide improved operability and ease of use, at least in certain patient types and/or certain clinical situations.

SUMMARY OF THE INVENTION

The present invention comprises a catheter assembly for draining and collecting fluid from a body cavity (e.g., the urinary bladder or gastrointestinal tract) of a mammal. The catheter assembly comprises a container, such as a flexible plastic bag, having an inner fluid containment space defined therewithin. A catheter passage opening is formed in the container or bag, at a first location, typically at one end thereof. A tip/lubricant reservoir member is mounted within the catheter passage opening, and is fused or attached to the container or bag. Such tip/lubricant reservoir has a hollow bore which extends longitudinally therethrough. An elongate tubular catheter, having a proximal end, a distal end, an outer surface of first outer diameter, and a hollow lumen extending longitudinally therethrough is initially positioned within the interior of the container or bag, with the distal end of the catheter being inserted into the hollow bore of the tip/lubricant reservoir. A quantity of lubricant is disposed within the sealed tip/lubricant reservoir. Thereafter, when it is desirable to insert the catheter into the body cavity, the catheter is advanced in the distal direction such that it punctures the tip/lubricant reservoir, with lubricant from the reservoir becoming deposited on the outer surface of the catheter. In this manner, the catheter may be inserted into the desired body cavity such that fluid from the body cavity will drain from the lumen of the catheter, and will become collected within the interior of the container (e.g., bag).

Further in accordance with the invention, an inflatable balloon or cuff may be formed on the outer surface of the catheter, near the distal end thereof, to retain the catheter within the urinary bladder or other intended anatomical location. Such inflatable balloon or cuff will enable the catheter to be utilized for long term indwelling use and continuous drainage of a desired body cavity.

Still further in accordance with the invention, the preferred container comprises a pliable bag formed of plastic (e.g., polyethylene) film, such bag having a proximal body portion of a first width $W_1$, and a distal chimney portion of a reduced with $W_2$. The tip/lubricant reservoir is mounted within a catheter passage opening formed in the distal end of the chimney portion of such bag. The chimney portion of the bag may be of an angular or tapered configuration such that its proximal base is of the reduced width $W_2$ and its distal end immediately adjacent the tip/lubricant reservoir is of a further reduced with $W_3$ which is even smaller than the reduced width $W_2$ at the basal end of the chimney portion of the bag. A grasping tab may be formed at a desired location on the chimney portion of the bag, and a perforated or tearable line may be formed across the chimney portion, immediately adjacent such grasping pad. In this manner, when it is desired to empty the bag, the user may grasp the grasping tab and may tear the chimney portion of the bag away, thereby facilitating emptying the contents of the bag into an appropriate container or drain. Grasping the grasping tab also facilitates controlled manipulation of the release orifice formed by tearing away the chimney portion, so as to facilitate easily controlled emptying of the contents of the bag.

Still further in accordance with the invention, the tip/lubricant reservoir member may be provided with at least a pair, preferably three, annular internal ribs through which the catheter passes. Such annular internal ribs will define a primary lubricant reservoir at the distal tips of the tip/lubricant reservoir member, a substantially cylindrical pre-lubricant reservoir space between the two distal-most annular internal ribs and an overflow chamber between the two proximal-most annular internal ribs. Lubricant contained within such pre-lubrication and primary reservoirs will become deposited upon the outer surface of the catheter as the catheter is advanced through the annular ribs, and the distal-most annular rib will operate to doctor or disperse the lubricant material over the outer surface of the catheter body such that a lubricant film of a desired thickness is evenly applied to the entire catheter. The two proximal-most annular internal ribs, which define the overflow chamber, mitigate overflowing of the lubricant from the pre-lubrication reservoir to the inner fluid containment space of the container. Frequently, it is desirable to prevent contamination of the contents of the container, since the contents of the container may be subject to analysis. As such, it is important to prevent the lubricant from entering the inner fluid containment space. Moreover, the overflow chamber defined by the two proximal-most annular internal ribs facilitates the collection of lubricant which leads past the second or middle annular internal rib, so as to prevent the lubricant from entering the inner fluid containment space of the container.

Still further in accordance with the invention, the lubricant contained within the pre-lubrication and primary reservoirs may comprise a silicone lubricant which resists desiccation and which has a shelf-life in dry storage in excess of three years. In particular, one such silicone lubricant is Dow Corning 360 Medical Lubricant, which has a dry storage shelf-life of approximately five years. The use of such silicone lubricant in the drainage catheter assemblies of the present invention permits shelf-storage of the drainage catheter assemblies for extended periods of time, such as more than four years, in contrast to drainage catheter assemblies of the prior art which have utilized water-based lubricant such as K-Y jelly having shelf storage lives in dry storage conditions of less than one year. The preferred Dow Corning 360 Medical Fluid Lubricant used in the drainage catheter assemblies of the present invention has a published shelf-life of sixty months when stored at or below 25° C.

Further objects and advantages of the invention will become apparent to those skilled in the art upon reading and understanding the following detailed description and the accompanying drawings.

DETAILED DESCRIPTION OF THE PREFERRED EMBODIMENTS

The following detailed description and the accompanying drawings are provided for the purpose of describing and illustrating presently preferred embodiments of the invention only, and are not intended to limit the scope of the invention in any way.

First Embodiment

FIGS. 1–7 show a first embodiment of a drainage catheter assembly 10 of the present invention.

Figure 1:
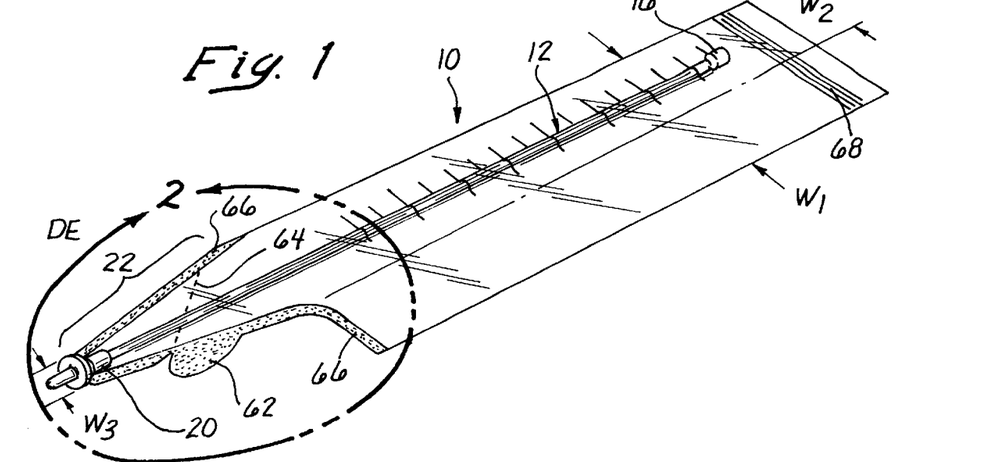
FIG. 1 is a perspective view of a first embodiment of a drainage catheter assembly of the present invention.

The drainage catheter assembly 10 comprises an elongate tubular catheter 12 and a pliable plastic containment bag 14.

The elongate tubular catheter 12 is initially disposed within the interior of the containment bag 14, and is subsequently advanceable in the distal direction DE to facilitate insertion of the catheter into a body passageway. For example, the catheter tube 12 may be inserted into the nose and downwardly through the esophagus to accomplish naso-gastric intubation. Similarly, the distal portion of the catheter tube 12 may be advanced into the urethra of a male or female patient to accomplish catheterization and drainage of urine from the urinary bladder.

Figures 2, 3:
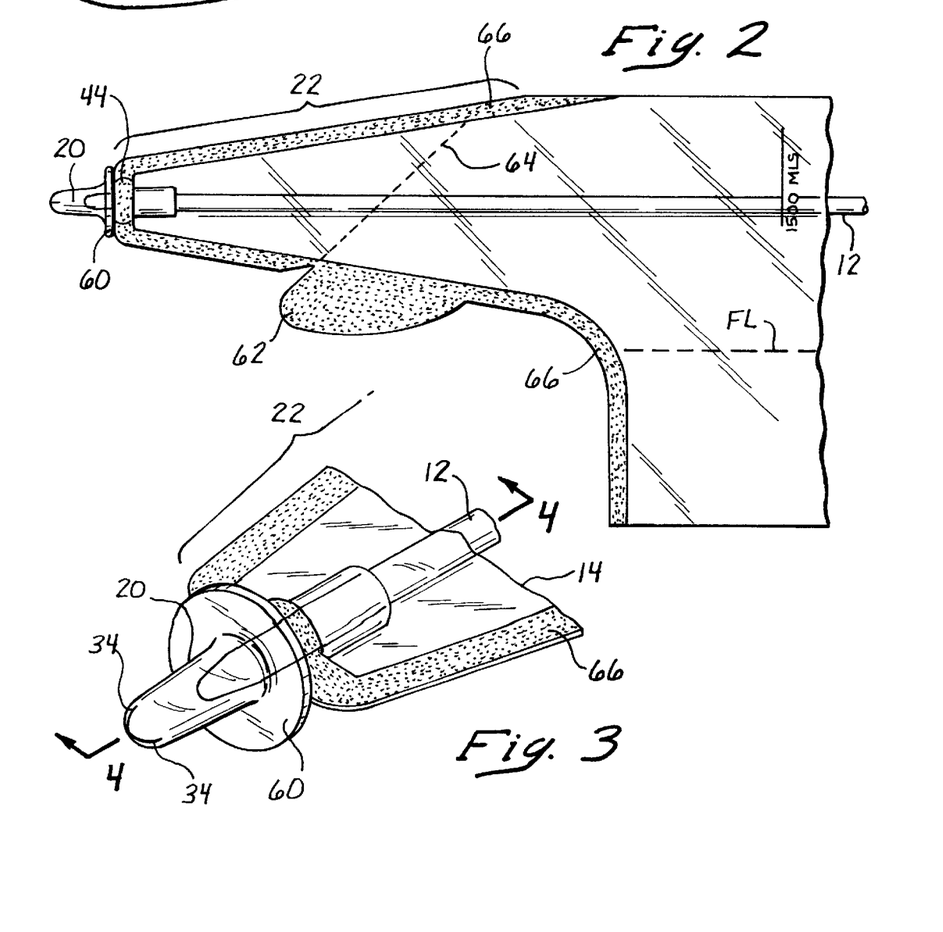
FIG. 2 is an enlarged view of one end of the drainage catheter assembly of FIG. 1.
FIG. 3 is an enlarged view of the tip of the drainage catheter assembly of FIG. 1.

The elongate tubular catheter 12 is of a first outer diameter $D_1$. A catheter retaining apparatus, such as a proximal engagement member 16 is formed on the tubular catheter 12 to prevent the catheter 12 from being fully extracted from, and separated from, the collection bag 14. The proximal engagement member 16 has an outer diameter $D_2$ which is larger than the outer diameter $D_1$ of the elongate tubular catheter body 12. A tapered shoulder 18 is formed on the forward or distal edge of the proximal engagement member 16. When the elongate catheter 12 is fully advanced in the distal direction, out of the containment bag 14, the annular shoulder 18 of the proximal engagement member 16 will abut against the proximal end of a stationary tip/lubricant reservoir 20 formed on the distal end of the chimney portion 22 of the containment bag 14. Such abutment of the proximal abutment member 16 against the stationary tip/lubricant reservoir 20 serves to prevent the tubular catheter 12 from being fully extracted and removed from the bag 14. In this regard, when the catheter 12 is fully advanced in its distal direction and inserted into a body passageway of a patient, body fluids which are drained through the lumen 13 of the catheter 12 will become collected in the collection bag 14.

Figure 7:
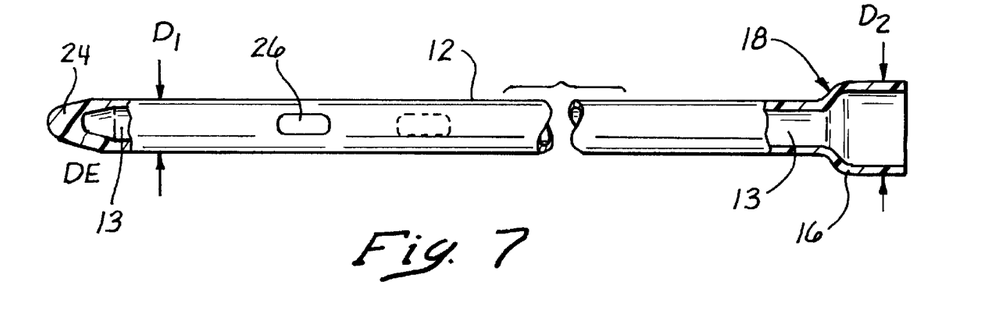
FIG. 7 is a side elevational/partially cut-away view of the catheter tube incorporated in the drainage catheter assembly shown in FIGS. 1–6.

The tubular catheter 12 has a blunt tapered or blunt-conical distal tip 24. A plurality of apertures 26 are formed in the sidewall of the catheter 12, near its distal tip 14, to permit body fluid and/or other matter to drain into the lumen 13 of the catheter 12.

Figures 4, 5, 6:
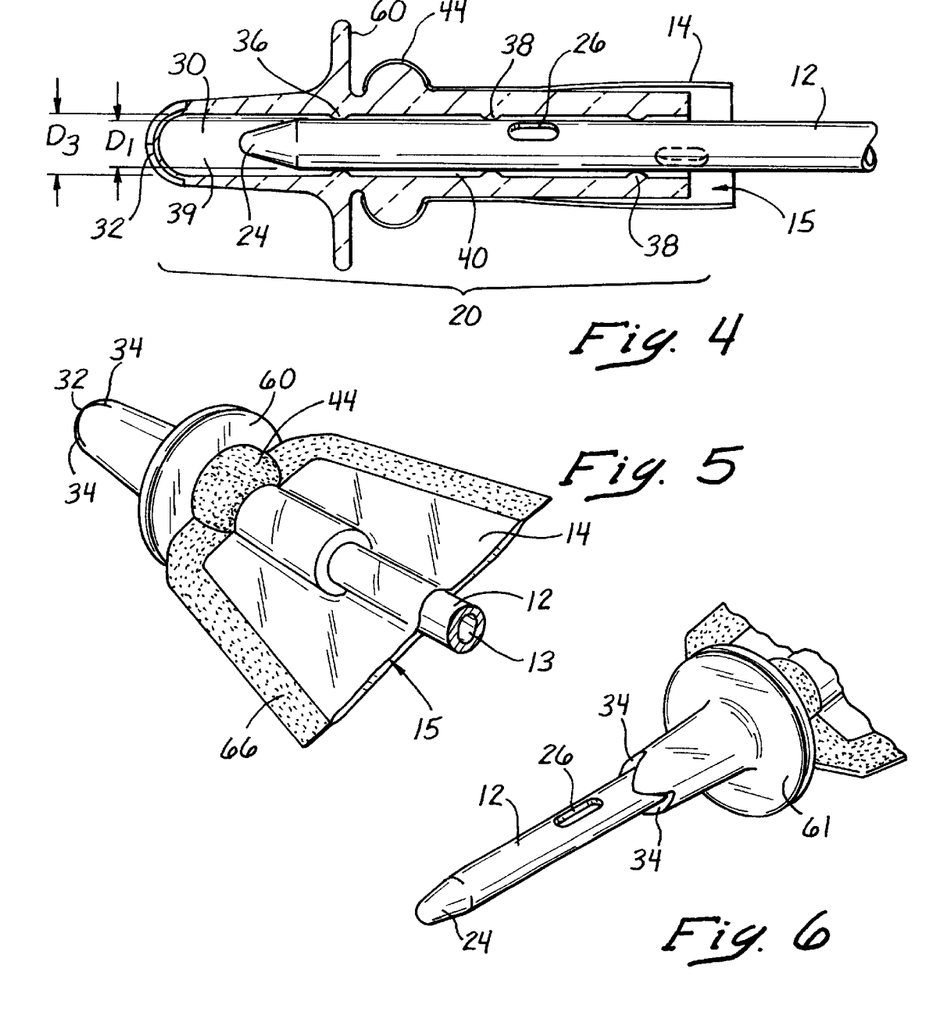
FIG. 4 is a longitudinal section view through line 4—4 of FIG. 3.
FIG. 5 is a rear perspective view of the distal catheter tip shown in FIG. 3.
FIG. 6 is a perspective view of the distal tip of the drainage catheter assembly shown in FIGS. 1–5 during distally-directed advancement of the catheter tube.

The tip/lubricant reservoir 20 is configured and constructed to facilitate firm sealing of the chimney portion 22 of containment bag 14 thereto, and to provide for even and continuous deposition of lubricant upon the outer surface of the catheter 12 as the catheter is advanced in the distal direction. The preferred design and construction of the tip/lubricant reservoir 20 is shown in FIGS. 4–6. As shown, the tip/lubricant reservoir 20 has a hollow inner bore or catheter passageway 30 extending longitudinally therethrough. A closed distal tip 32, is formed on the distal end of the hollow bore 30 and is provided with one or more catheter penetrable openings 34, such as self-sealing slit(s) or disruptable perforations, to permit the blunt distal tip 24 of the catheter 12 to penetrate through the distal tip 32 of the tip/lubricant reservoir 20. In the preferred embodiment shown, two (2) crossed slits 34 are partially pre-cut in elastomeric material of the distal tip 32, as shown. Such partial cuts do not extend through the full thickness of the tip 32, but rather penetrate only sufficiently to allow easy puncturing by the distal tip 24 of the catheter 12.

Use of such a partially pre-cut or perforated distal tip 32 allows maintenance of the catheter in a sterile condition right up until the time immediately prior to which the catheter is forced therethrough. In this manner, the catheter creates a passageway through the distal tip 32 immediately prior to use. By way of contrast, contemporary catheters commonly allow undesirable non-sterile touching or atmospheric contact with the distal end of the catheter.

As shown in FIG. 4, the thickness of the material of which the tip/lubricant reservoir 20 is formed may be lessened or diminished in the region of distal tip 32 to facilitate such penetration of the distal catheter tip 24 therethrough. An annular flange 60 is preferably formed about the tip/lubricant reservoir 20, as shown.

The individual components of the catheter assembly 10 may be formed of any suitable materials. In the presently preferred embodiments shown in the drawings, the containment bag 14 may be formed of low density polyethylene film having a thickness of approximately 0.003 inch such as that sold under the trademark PETROTHENE PE 4955 B available commercially from Quantum Chemical Corporation, Rolling Meadows, Ill. The catheter 12 may be formed of polyvinyl chloride tubing such as that commercially available from Kelcourt Plastics, Inc., San Clemente, Calif. The tip member/lubricant reservoir 20 may be formed of a pliable silicone material. The lubricant contained within the tip member/lubricant reservoir is preferably polydimethysiloxane fluid, such as DOW CORNING 360 Medical Fluid available commercially from Dow Corning Corporation, Midland, Mich., preferably having a viscosity at 25° C. of approximately 350 centistokes.

The inner bore 30 of the tip/lubricant reservoir 20 has a diameter $D_3$ which is larger than the outer diameter $D_1$ of the catheter 12. First, second and third annular rib members 36, 38, 38' are formed around the inner surface of the longitudinal bore 30 of the tip/lubricant reservoir 20, at spaced-apart locations as shown in FIG. 4. The innermost surfaces of these annular rib members 36, 38, 38' are smaller than the inner diameter $D_3$ of the inner bore 30 but still slightly larger than the outer diameter $D_1$ of the catheter 12. In this manner, the annular rib members 36, 38, 38' abut against or are close-spaced away from the outer surface of the catheter 12 as the catheter is longitudinally advanced through the bore 30 of the tip/lubricant reservoir 20.

A primary lubricant reservoir 39 is defined within the distal-most portion of the inner bore 30 between the tip 32 and the first annular rib member 36. A pre-lubrication reservoir is formed within the bore 30 between the first annular rib member 36 and the second annular rib member 38. In a similar fashion, a lubricant overflow reservoir is defined within the bore 30 between the second annular rib member 38 and the third annular rib member 38'. A lubricant overflow reservoir is defined between annular rib members 38 and 38'. A quantity of flowable lubricant is initially deposited within the cylindrical lubricant space 40 at the time of fabrication or manufacture of the catheter assembly 10. Thereafter, when the pliable catheter 12 is advanced in the distal direction, the blunt distal tip 24 of the catheter 12 will penetrate through the catheter-penetrable distal tip 32 of the tip/lubricant reservoir 30, and further such that the lubricant material contained within the cylindrical lubricant space 40 becomes evenly distributed in a thin film upon the advancing outer surface of the catheter 12.

The apertures 26 are preferably formed within the tubular catheter 12 such that they are proximal of annular rib member 38, so as to prevent plugging of the apertures 26 with lubricant.

The outer surface of the tip/lubricant reservoir 20 incorporates an annular enlargement 44 which serves to promote fusion or sealing of the material of the collection bag 14 to the neck of the tip/lubricant reservoir 20. In this regard, the top edge of the chimney portion 22 of the collection bag 14 is positioned immediately forward of the annular enlargement or ring 44 and the material of the bag is laminated, heat fused, adhered, or otherwise affixed to the outer surface of the annular enlargement 44, as shown in FIGS. 4 & 5. In this manner, the annular enlargement 44 formed on the outer surface of the distal tip member/lubricant reservoir 20 forms a fusion zone whereupon the material of the collection bag 14 may be firmly fused and/or otherwise affixed to the neck of the distal tip member/lubricant reservoir 20. In this manner, the distal tip member/lubricant reservoir 20 is stationarally affixed to the opening formed at the top end of the chimney portion 22 of the collection bag 14.

It will be appreciated that the containment bag 14 may be of any suitable size and shape. In the preferred embodiment shown in the drawings, the containment bag 14 has a lower portion of a first width $W_1$, and an upper chimney portion 22 which, at its basal end, has a width $W_2$ which is approximately one half of the full width $W_1$ of the lower portion of the bag. The chimney portion 22 preferably tapers to a distal end width $W_3$ which is only slightly wider than the diameter of the annular flange 60 formed on the tip member/lubricant reservoir 20.

A graspable tear tab 62 is formed on one side of the chimney portion 22 of the bag 14, immediately below a traversing perforation 64. The traversing perforation 64 forms a weakened line across the chimney 22 of the bag 14 such that, when it is desired to obtain a sample of the fluid collected within the bag 14, the user may grasp the tear tab 62, and tear the chimney 22 of the bag 14 across the perforated tear line 64, thereby detaching the distal-most portion of the chimney 22 of the bag, and providing an opening through which a sample of fluid contained in the bag may be decanted or poured.

The perforations 64 only partially penetrate the thickness of the bag 14, such that they make tearing therealong easy, but do not cause undesirable leakage from the bag 14 prior to such tearing.

The tear tab 62 and perforations 64 thus facilitate emptying of the bag 14. Such emptying of the bag may be useful when a sample of the fluid contained therein is desired. Accurate control of the fluid being so emptied from the bag 14 is facilitated by the chimney 22 which may be grasped therearound by the human hand, so as to restrict the flow of fluid from the bag 14, as desired. Thus, the chimney portion 22 of the bag 14 defines a neck or spout which may be grasped by the user's hand and squeezed so as to provide for controlled dispensing of the fluid contained within the bag 14.

Second Embodiment

FIGS. 8, 9, 9a and 10c show a second embodiment of the catheter assembly 10a. This second embodiment of the catheter assembly 10a comprises a catheter 12a, collection bag 14a and distal tip member/lubricant reservoir 20a which are the same as described hereabove with respect to the first embodiment of the catheter assembly 10. However, this second embodiment of the catheter assembly 10a further incorporates an annular inflatable balloon 50 mounted upon the outer surface of the catheter 12 at a spaced distance X from the distal tip of the catheter 12a. A balloon inflation lumen 52 is formed within the body of the catheter 12a, and a balloon inflation tube 54 extends from the proximal end of the catheter 12a to permit infusion/withdrawal of inflation fluid into/out of the balloon 50.

The balloon inflation lumen 52 may be formed by any suitable means. For example, the balloon inflation lumen 52 may comprise a separate tube which extends longitudinally through the lumen 13a of the catheter 12a. Alternatively, in the embodiment shown in FIGS. 9–9a, the balloon inflation lumen 52 comprises a partitioned off segment of the main catheter lumen 13a, and is defined by a bulkhead member 61 which extends longitudinally through the catheter body 12a so as to divide the main catheter drainage lumen 13a from the balloon inflation lumen 52.

Figures 8, 9, 9A:
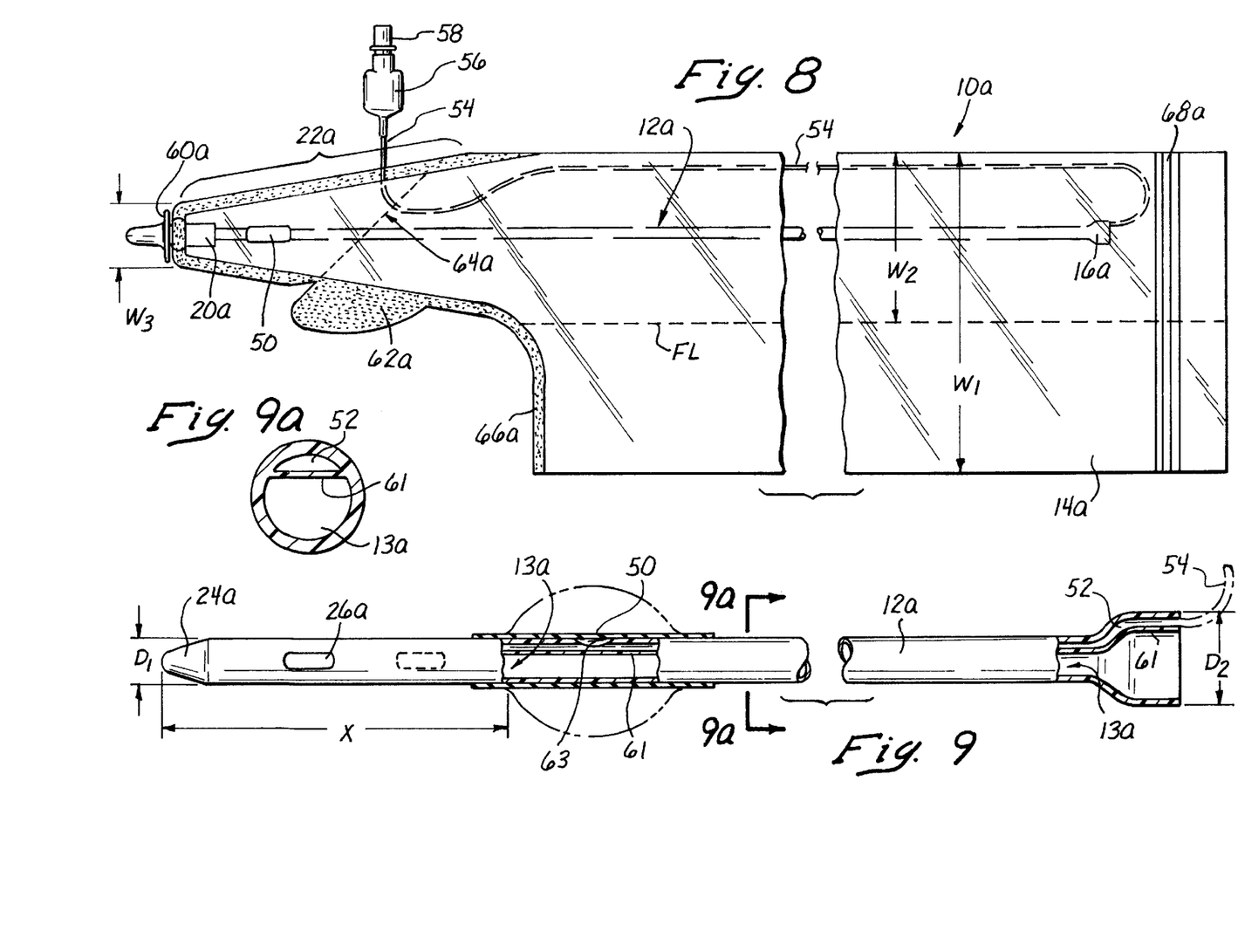
FIG. 8 is a side elevational view of a second embodiment of a drainage catheter assembly of the present invention, having an inflatable cuff formed on the catheter tube for retaining the catheter tip within the urinary bladder or other anatomical structure.
FIG. 9 is a side elevational/partially cut-away view of the catheter tube incorporated in the drainage catheter assembly of FIG. 8.
FIG. 9a is a cross sectional view through line 9a-9a of FIG. 9.

An inflation fluid port 63 is formed in the catheter body 12a between the balloon inflation lumen 52 and the interior of the balloon 50. In this regard, balloon inflation fluid may be passed distally through the balloon inflation lumen 52 and outwardly through the balloon inflation fluid port 63 to facilitate inflation of the balloon 50. Thereafter, such balloon inflation fluid may be withdrawn inwardly through the inflation fluid port 63 and in the proximal direction out of the inflation fluid lumen 52.

To facilitate the infusion/withdrawal of balloon inflation fluid, a pliable balloon inflation tube 54 is fused, heat-sealed, adhered or otherwise attached to the proximal end of the balloon inflation lumen 52. A pressure-distensible inflation indicator sac 56 is mounted on the proximal end of the balloon inflation tube 54 and a connector 58, such as a valved Luer connector, is incorporated into or connected to such inflation fluid sac 56. In this manner, a syringe may be attached to the connector 58, and a balloon inflation fluid (e.g., air, saline solution, etc.) may be infused from the syringe, through the connector 58, through the inflation fluid tube 54, through the inflation fluid lumen 52, out of the inflation fluid port 63 and into the balloon 50. When sufficient inflation pressure is reached within the interior of the balloon 50, the inflation indicator sac 56 will be distended and visibly filled with inflation fluid. On the other hand, when insufficient inflation pressure is contained within the balloon 50 the indicator sac 56 will be visibly flaccid or deflated. In this manner, the inflation fluid indicator sac 56 will serve as a visual indicator of the inflation status of the balloon 50.

When it is desired to deflate the balloon, the plunger of the syringe attached to the connector 58 will be withdrawn, thereby drawing inflation fluid in the proximal direction from the balloon 50, throughout inflation fluid port 63, in the proximal direction through inflation fluid lumen 52 and inflation fluid tube 54, and the connector 58. When the balloon has reached its fully deflated condition, the inflation indicator sac 56 will be flaccid and deflated, thereby serving as a visual indicator that the balloon 50 has been fully deflated.

The connector 58 may incorporate a check valve or valving apparatus of the type well known in the art to permit fluid to be infused and withdrawn through tube 54 so long as a syringe is attached to the connector be fitted with an external stop cock or other suitable type of closure apparatus such that, when the syringe is detached from the valve Luer connector 58, the Luer connector 58 will close-off thereby preventing inadvertent leakage of fluid out of the balloon 50.

Manufacturing of the Catheter Assembly

The preferred catheter assemblies 10, 10a of the present invention, as described hereabove, may be manufactured by any suitable means. In the preferred embodiments shown, the containment bag 14, 14a is initially formed from a tube formed of polyethylene film having a thickness of approximately 0.003 inch and a width $W_1$. The outline of the tapered chimney portion 22, 22a and graspable tab member 62, 62a are then cut out of such polyethylene film tube. The tip/lubricant reservoir 20 is then inserted to its desired position and a heat lamination process is utilized to form the peripheral lamination 66 (e.g, heat seal) around the outer edges of the chimney portion 22, 22a and grasping tap 62, 62a, as shown. A perforation tool may then be used to form the partially perforated tear line 64, 64a diagonally across the chimney portion 22, 22a of the containment bag 14, 14a, preferably in alignment with the diagonal distal edge of the grasping tab 62, 62a, as shown. The perforation tear line 64, 64a may be formed by either forming a series of perforations or forming a single continuous cut. In either case, the perforations or cut are formed such that they do not completely penetrate the wall of the bag 14, 14a, so as to prevent undesirable leakage of fluid from the bag 14, 14a.

It will be appreciated, that the heat lamination process utilized to form the peripheral lamination 66, 66a about the outer edge of the chimney portion 22, 22a of the bag 14, 14a will also securely fuse the distal end of the chimney portion 22, 22a to the annular enlargement 44 formed on the tip/lubricant reservoir 20, 20a. In this manner, the tip/lubricant reservoir 20, 20a will be firmly affixed to the distal end of the containment bag 14, 14a with the annular flange 60, 60a of the tip/lubricant reservoir 20, 20a being adjacent the distal end of the chimney portion 22, 22a of the bag 14, 14a.

The catheter 12, 12a is then inserted into the interior of the containment bag 14, 14a and the distal end of the catheter is advanced into the tip/lubricant reservoir 20, 20a such that the blunt distal tip 24, 24a of the catheter is distal to the first or distal-most annular rib 36 formed within the tip/lubricant reservoir 20, 20a. Thereafter, a proximal lamination 68, 68a (e.g., heat seal) is formed across the proximal portion of the containment bag 14, 14a, immediately behind the proximal end of the catheter 12, 12a. This proximal lamination 68, 68a serves to prevent the catheter 12, 12a from retracting in the proximal direction such that the distal tip 24, 24a of the catheter 12, 12a could escape from its intended position wherein the body of the catheter protrudes past the first annular rib 36 of the tip/lubricant reservoir 20. In this manner, the desired longitudinal positioning of the catheter 12, 12a is maintained, with the distal end of the catheter being resident within the bore 30 of the distal tip member 20, 20a during packaging and shipment of the catheter assembly 10, 10a.

According to the preferred embodiment of the present invention, the lubricant, preferably a silicone lubricant such as polydimethysiloxane (e.g., DOW CORNING 360 Medical Fluid, The Dow Chemical Company, Midland, Mich.) is deposited within the primary reservoir 39 prior to advancing the catheter 12, 12a into the tip/lubricant reservoir 20, 20a. Additional lubricant, again preferably a silicone lubricant such as DOW CORNING 360 Medical Fluid, is subsequently added to the pre-lubrication reservoir 40 utilizing a syringe. Those skilled in the art will appreciate that various other means for dispensing lubricant into the primary 39 and pre-lubrication 40 reservoirs are likewise suitable.

Figures 10, 10A:
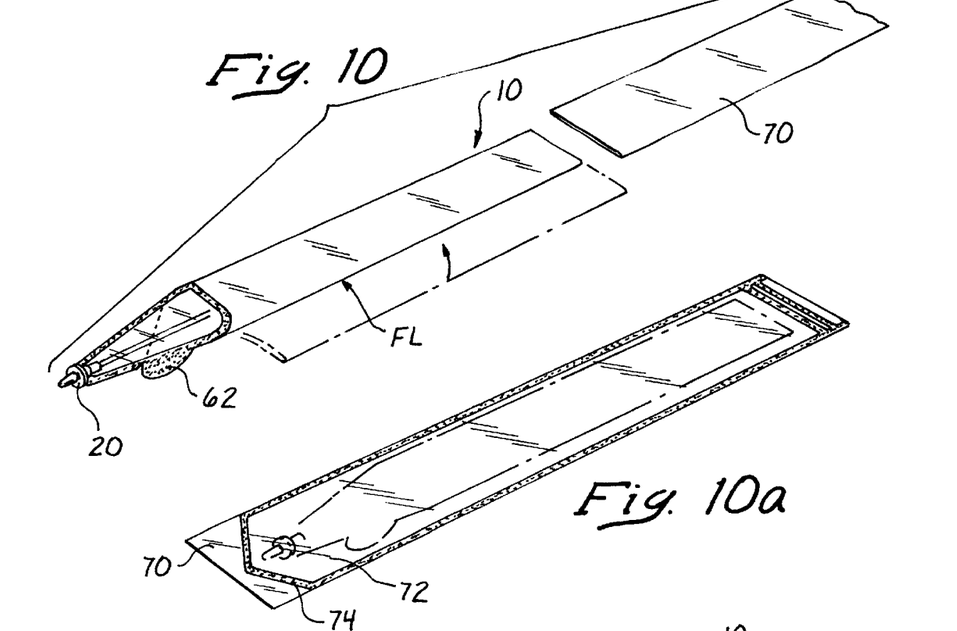
FIG. 10 is a perspective view of a method by which the drainage catheter assemblies shown in FIGS. 1–9 may be folded to facilitate packaging thereof.
FIG. 10a is a partial perspective view of a preferred packaging envelope of the present invention containing a drainage catheter assembly of the present invention folded in the manner shown in FIG. 10.
Figure 10B:
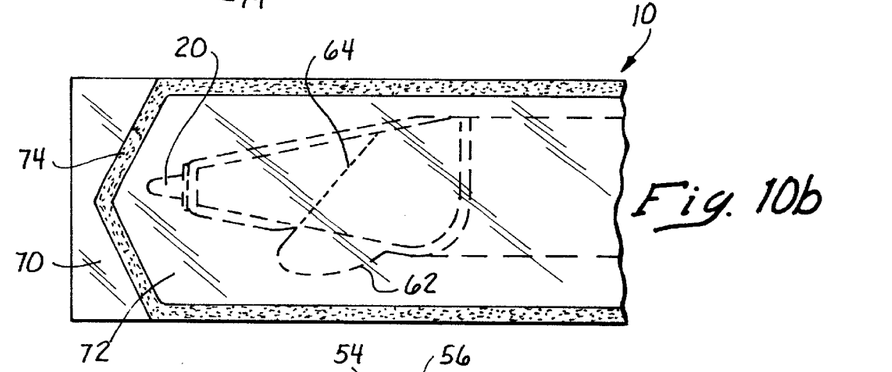
FIG. 10b is a partial elevational view showing a packaging envelope of the present invention containing a drainage catheter assembly of the first embodiment, folded in the manner shown in FIG. 10.
Figure 10C:
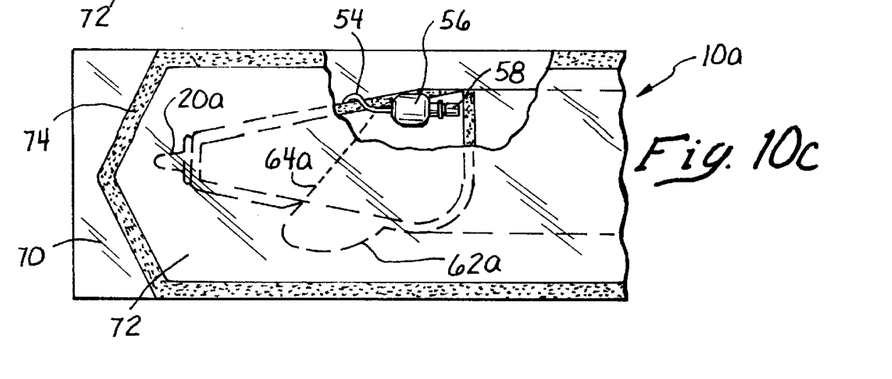
FIG. 10c is a partial elevational view showing a packaging envelope of the present invention containing a drainage catheter assembly of the second embodiment, folded in the manner shown in FIG. 10.

The preferred method of packaging the catheter assembly 10, 10a, is by initially folding the containment bag 14, 14a along an imaginary fold line FL which projects longitudinally down the approximate longitudinal midpoint of the proximal portion of the containment bag 14, 14a, as shown in FIG. 10. Thereafter, the folded catheter assembly 10, 10a is inserted into a pouch comprised of spunbonded polyolefin (uncoated) such as 1059 B Tyvek, Manufactured by Mangar Industries, Inc. of New Britain, Pa., preferably having a thickness of approximately 0.0067 inch, defining a base card or sheet 70, and a preferably transparent top sheet 72, preferably comprised of a material such as 0.0048 inch polyester/0.002 low density polyethylene, such as NP-110, manufactured by Mangar Industries, Inc. of New Britain, Pa. The top sheet 72 is fused, about its periphery, to the base sheet 70 such that a peripheral lamination or seal 74 is formed therearound. In this manner, the catheter assembly 10, 10a is securely enclosed within an envelope or blister pack which is substantially impervious to contaminants or microbiological pathogens.

Use and Operation of the Preferred Catheter Assemblies

In routine operation, the catheter assembly 10, 10a will be removed from its package, and the urethral meatus of the patient will be cleansed utilizing an appropriate antiseptic solution. The person inserting the catheter will then grasp the catheter assembly 10, 10a proximal to the annular flange 60, 60a of the tip/lubricant reservoir 20, 20a, and will position the closed distal tip 32 of the tip/lubricant reservoir 20, 20a immediately adjacent the urethral meatus of patient.

Thereafter, the catheter 12, 12a will be grasped through the containment bag 14, 14a and will be advanced in the distal direction such that the distal tip 24 of the catheter 12, 12a passes through the partially formed slits 34 at the distal tip 32 of the tip/lubricant reservoir 20, 20a and into the urethra of the patient. Thereafter, the catheter 12, 12a is further advanced, approximately 2 inches at a time, until the apertures 26 formed in the side wall of the catheter 12, 12a are positioned within bladder of the patient, and urine begins to flow through the lumen 13, 13a of the catheter and into the containment bag 14, 14a. As the catheter 12, 12a is advanced through tip/lubricant reservoir 20, 20a, lubricant is first applied thereto from the pre-lubrication reservoir 40 and then further lubricant is applied thereto from the primary lubricant reservoir 39, so as to assure a generally even and adequate quantity of lubrication is applied thereto.

Thereafter, the bag may be retracted until the proximal engagement member 16, 16a formed on the proximal end of the catheter 12, 12a engages or abuts against the proximal end of the distal tip/lubricant reservoir 20, 20a, and the bag 14, 14a may be attached to an appropriate hanging apparatus such that urine flow may continue to collect within the bag 14, 14a.

It will be appreciated that, as mentioned above, as the catheter 12, 12a is advanced into the urethra of the patient, lubricant contained within both the pre-lubrication reservoir 40 and the primary lubricant reservoir 39 will become deposited on the outer surface of the catheter, 12, 12a and will serve to assure adequate lubrication of the catheter.

When the catheter is intended to remain indwelling for a period of time, the second embodiment of the invention shown in FIGS. 8–9 will typically be utilized. When such second embodiment of the catheter assembly 10a is utilized, a syringe will be connected to the balloon fluid infusion port 58 and will be utilized to inflate the balloon 50 while it is located within the patient's bladder. When so inflated, the balloon 50 will be prevented from being retracted out of the bladder, and the catheter 12a will thus remain indwelling within the bladder for the desired period of time.

Thereafter when it is desired to remove the catheter, a syringe will again be attached to the balloon fluid inflation port 58 and will be utilized to withdraw the inflation fluid from the balloon, thereby deflating the balloon and permitting the catheter 12a to be withdrawn from the patient.

In either embodiment of the invention, the bag 14, 14a may be emptied by grasping the grasping tab 62, 60a and tearing the chimney 22, 22a of the bag away at the perforated tear line 64, 64a. Thereafter, the torn-away chimney portion 22, 22a of the bag 14, 14a with the catheter 12, 12a attached thereto may be discarded, and the remaining proximal portion of the bag may be emptied, or aliquot of urine may be decanted into sample containers for subsequent laboratory analysis or retention.

It will be appreciated that the invention has been described hereabove with reference to certain presently preferred embodiments only, and no effort has been made to exhaustively describe all possible embodiments in which the invention may take form. Indeed, various additions, deletions, modifications and alternations may be made to the above-described embodiments without departing from the intended spirit and scope of the invention. Accordingly, it is intended that all such additions, deletions, alterations and modifications be included within the scope of the following claims.

What is claimed is:

1. A catheter assembly for draining and collecting fluid from a body cavity, said assembly comprising:

a container having an inner containment space defined therewithin, said container having a fluid reservoir portion and a chimney portion which extends from said fluid reservoir portion, said fluid reservoir portion having a first width and said chimney portion having a second width which is less than said first width;

a catheter passage opening formed in the chimney portion at a first location;

a tip member/lubricant reservoir mounted to the catheter passage opening, said tip member/lubricant reservoir having:

i) a hollow bore extending longitudinally therethrough, said hollow bore having an inner surface of a diameter which is larger than the outer diameter of the catheter;

ii) a first annular rib extending inwardly from the inner surface of the bore of the tip member/lubricant reservoir defining a first lubricant reservoir space distal thereof, said first annular rib having an inner diameter which is smaller than the inner diameter of the hollow bore, but larger than the outer diameter of the catheter, and, a quantity of lubricant being disposed within said first lubricant reservoir space;

said catheter being initially positioned within the inner containment space of the container such that a portion of the catheter extends through said chimney and into the bore of the tip member/lubricant reservoir, the catheter being thereafter advanceable in a distal direction through the first annular rib such that the distal end of the catheter will become projected out of the tip member/lubricant reservoir and a layer of lubricant will be deposited on the outer surface of the catheter, the thickness of said layer of lubricant being regulated by the inner diameter of the first annular rib.

2. The catheter assembly of claim 1 wherein the tip member/lubricant reservoir has a closed distal tip through which the distal end of the catheter will penetrate as the catheter is advanced in the distal direction.

3. The catheter assembly of claim 2 wherein the closed distal tip of the tip member/lubricant reservoir has at least one slit formed therein to permit the catheter to penetrate therethrough, said slit(s) only partially penetrating the tip member/lubricant reservoir, so as to prevent lubricant leakage therefrom and so as to maintain sterility thereof prior to use.

4. The catheter assembly of claim 1 wherein the quantity of lubricant disposed within the lubricant reservoir space of the tip member/lubricant reservoir comprises silicone lubricant.

5. The catheter assembly of claim 4 wherein the lubricant is a non-water-based lubricant having a shelf storage life of at least three years.

6. The catheter assembly of claim 4 wherein the lubricant comprises polydimethysiloxane.

7. The catheter assembly of claim 1 further comprising a second annular rib similar to said first annular rib and formed proximally with respect thereto, so as to define a second lubricant reservoir space.

8. The catheter assembly of claim 7 wherein the first annular rib member of the tip member/lubricant reservoir has an inner diameter which is 0.5 mm larger than the outer diameter of the catheter, and wherein said first annular rib further causes a thin film of lubricant of 0.25 mm thickness to be deposited from said second lubricant reservoir space onto the outer surface on the catheter as the catheter is advanced therethrough.

9. The catheter assembly as recited in claim 1, wherein said tip member/lubricant reservoir further comprises a third annular rib similar to said second annular rib and formed proximally with respect thereto, so as to define a lubricant overflow chamber between said second annular rib and said third annular rib.

* * * * *